(12) United States Patent
Li

(10) Patent No.: US 8,359,164 B2
(45) Date of Patent: Jan. 22, 2013

(54) SUPERVISED PRINCIPAL COMPONENT ANALYSIS

(76) Inventor: Weiyong Li, Doylestown, PA (US)

( * ) Notice: Subject to any disclaimer, the term of this patent is extended or adjusted under 35 U.S.C. 154(b) by 0 days.

(21) Appl. No.: 13/037,851

(22) Filed: Mar. 1, 2011

(65) Prior Publication Data

US 2011/0216313 A1 Sep. 8, 2011

Related U.S. Application Data

(60) Provisional application No. 61/309,773, filed on Mar. 2, 2010.

(51) Int. Cl.
*G06F 19/10* (2011.01)
*G01N 24/00* (2006.01)

(52) U.S. Cl. .......................... 702/19; 436/173

(58) Field of Classification Search .................. None
See application file for complete search history.

(56) References Cited

U.S. PATENT DOCUMENTS

| 6,853,923 | B2 | 2/2005 | Trygg et al. |
| 6,871,169 | B1 | 3/2005 | Hazen et al. |

OTHER PUBLICATIONS

Rodionova et al. (Analytica Chimica Acta (2005) vol. 549, pp. 151-158).*
Corti et al. (Analyst (1999) vol. 124; pp. 755-758).*
El-Hagrasy et al. (Journal of Pharmaceutical Sciences (2001) vol. 90, pp. 1298-1307).*
Fountain et al. (Journal of Pharmaceutical and Biomedical Analysis (2003) vol. 33, pp. 181-189.*
Lyon et al. (AAPS PharmSciTech (2002) vol. 3, pp. 1-15).*
Reich et al. (Advanced Drug Delivery Reviews (2005) vol. 57, pp. 1109-1143).*
Roggo et al. (Journal of Pharmaceutical and Biomedical Analysis (2007) vol. 44, pp. 683-700.*
Thosar et al. (Pharmaceutical Development and Technology (2001) vol. 6, pp. 1-12).*

* cited by examiner

*Primary Examiner* — Lori A Clow
(74) *Attorney, Agent, or Firm* — Sinorica, LLC

(57) ABSTRACT

The invention provides a multivariate modeling method for quantitative analysis by supervised principal component analysis (SPCA). The method comprises: (a) designing a plurality of calibration samples wherein the desired variances are dominant or greatly enhanced; (b) producing a calibration data matrix using suitable mathematical pretreatment and truncation of the acquired NIR/Raman spectra of the calibration samples; (c) decomposing the matrix using PCA; (d) evaluating the score and loading matrices to ensure a genuine orthogonal relationship between scores of the desired latent variables in a two-dimensional principal component space 7; (e) generating a prediction matrix for quantitative prediction of unknown samples. This method does not require testing of calibration samples using a reference method. In addition, this method has high tolerance to variations in sample composition and manufacturing conditions.

19 Claims, 12 Drawing Sheets

| Calibration Tablets | | | |
|---|---|---|---|
| | *DC70* | *DC100* | *DC130* |
| CP01 | 10 | 10 | 10 |
| CP02 | 10 | 10 | 10 |
| CP03 | 10 | 10 | 10 |
| CP04 | 10 | 10 | 10 |
| CP05 | 10 | 10 | 10 |

CP = Compression force; DC = drug concentration

FIG. 11

SUPERVISED PRINCIPAL COMPONENT ANALYSIS

The current application claims a priority to the U.S. Provisional Patent application Ser. No. 61/309,773 filed on Mar. 2, 2010.

FIELD OF INVENTION

The invention relates generally to the field of fast and non-destructive analysis of solid samples, which include but are not limited to pharmaceutical powders and tablets, by near infrared spectroscopy/Raman spectroscopy and multivariate modeling.

BACKGROUND OF THE INVENTION

Near infrared spectroscopy (or Raman spectroscopy) has been widely used in pharmaceutical development as quality and process control methods. Two types of methods are generally used, i.e. qualitative and quantitative methods. Qualitative methods are used for identification of drug substances, excipients and other raw materials as well as final products whereas quantitative methods are for determination of drug concentration, moisture content and other product attributes. Both types of methods require multivariate calibration models.

To develop NIR/Raman methods for determining drug content (content uniformity or CU) in tablets, a quantitative relationship between the NIR/Raman spectra and drug concentration is established by multivariate modeling. A common approach is by means of partial least squares (PLS) regression. It is well known that the total variance in the NIR/Raman data set is attributed not only to drug concentration variation but also to variations of excipient concentration, moisture content, tablet density and others. In addition, Trygg et al. have pointed out in U.S. Pat. No. 6,853,923 that "For solid samples, this systematic variation is due to, among others, light scattering, and differences in spectroscopic path length, and may often constitute the major part of the variation of the sample spectra". Furthermore, "the variation in X (matrix of spectral data) that is unrelated to Y (matrix of drug concentration) may disturb the multivariate modeling and cause imprecise predictions for new samples and also affect the robustness of the model over time". To address this issue, Trygg et al. proposed a so called Orthogonal Partial Least Squares (QPLS) method to remove the systematic variation from X through orthogonalizing the X matrix and removing the irrelevant variances. Advantage of the QPLS method compared with the other pretreatment methods is that it keeps the Y-relevant variances intact.

Hazen et al. proposed another different variant of multivariate modeling in U.S. Pat. No. 6,871,169, which was called Combinative Multivariate Calibration (CMC). In their method, the analytical signals were separated into different wavelength or spectral regions. Then each region was modeled independently using different number of factors. This approach "allows for each wavelength or spectral region to be modeled with just enough factors to fully model the analytical signal without the incorporation in the model of noise by using excess factors". The data pretreated by CMC can be used for further partial least squares regression or principal component regression (PCR).

Principal component analysis (PCA) is widely used as an unsupervised and exploratory algorithm for multivariate data analysis. PCA does not make assumptions about an underlying causal model. It is simply a variable reduction algorithm that utilizes a relatively small number of latent variables 6 (also called principal components or PCs) to represent most of the variances in a set of observed variables. On the other hand, PCA does assume linearity in analysis of spectral data. It also ranks the latent variables, which are orthogonal to each other, based on the amount of variances that they describe. These characteristics imply that conventional PCA is not suitable for determining active drug content in pharmaceutical tablets because of the following: (a) the variance that is related to drug concentration may be masked by noise; (b) the variance that is related to drug concentration may not have a high enough ranking; (c) the relationship between latent variables, wherein at least one latent variable is related to the drug concentration, may not be genuinely orthogonal; (c) the ranking of the latent variable that is related to the drug concentration may not be consistent among different data sets.

SUMMARY OF THE INVENTION

This invention discloses the use of supervised principal component analysis (SPCA) to overcome the above mentioned shortcomings of the conventional PCA in quantitative analysis of pharmaceutical samples. The intention is to use SPCA to replace the conventional HPLC method to save development time and cost. The concept contains three basic elements: (a) to promote rank of the latent variable of interest by using a plurality of calibration samples (b) to ensure genuine orthogonality among latent variables of interest by using properly designed calibration samples, suitable pretreatment and wavelength range/region; (c) to facilitate quantitative analysis of unknown samples by forming a prediction set.

Upon completion for preparation of calibration samples, acquiring the NIR spectra and data pretreatment using appropriate chemometric algorithms, PCA is then performed to decompose the X matrix to obtain the corresponding loading (P) and score (T) matrices according the following equation:

$$X = TP' + E$$

where E is the residual matrix. The subsequent tasks are to identify the correct latent variable that describes the variation of drug concentration in the calibration samples, followed by evaluation of the score matrix to see if the orthogonality among latent variables is genuine. If the genuine orthogonality has been achieved, the SPCA method can be used for analysis of unknown samples by forming a prediction data set. Otherwise, a different wavelength region and/or range have to be selected, or even a new calibration sample set has to be designed and prepared.

ADVANTAGEOUS EFFECT OF THE INVENTION

The present invention has advantages over the most widely used PLS regression method that models variances not only from active drug but also from excipients and many other sources. Therefore PLS models are sensitive to changes in physical and chemical properties of the raw materials as well as the final product. This is the reason why PLS method has not been widely used in supporting early stage pharmaceutical product and process development. On the contrary, the SPCA approach separates the active drug related variance from all the other variances, which makes it particularly suitable in early stage product development. In addition, calibration samples can be easily prepared in a laboratory setting without putting too much emphasizes on matching the manufacturing conditions. Another added advantage is that usually reference testing is not necessary. Therefore the calibration samples can be saved and spectra can be acquired on different brands of instruments. The concern of model transfer between instruments and manufacturing sites are minimized or eliminated.

BRIEF DESCRIPTION OF THE DRAWINGS

FIG. 11 is a calibration table for the tablets.

DETAIL DESCRIPTION OF THE INVENTION

Figure 1:
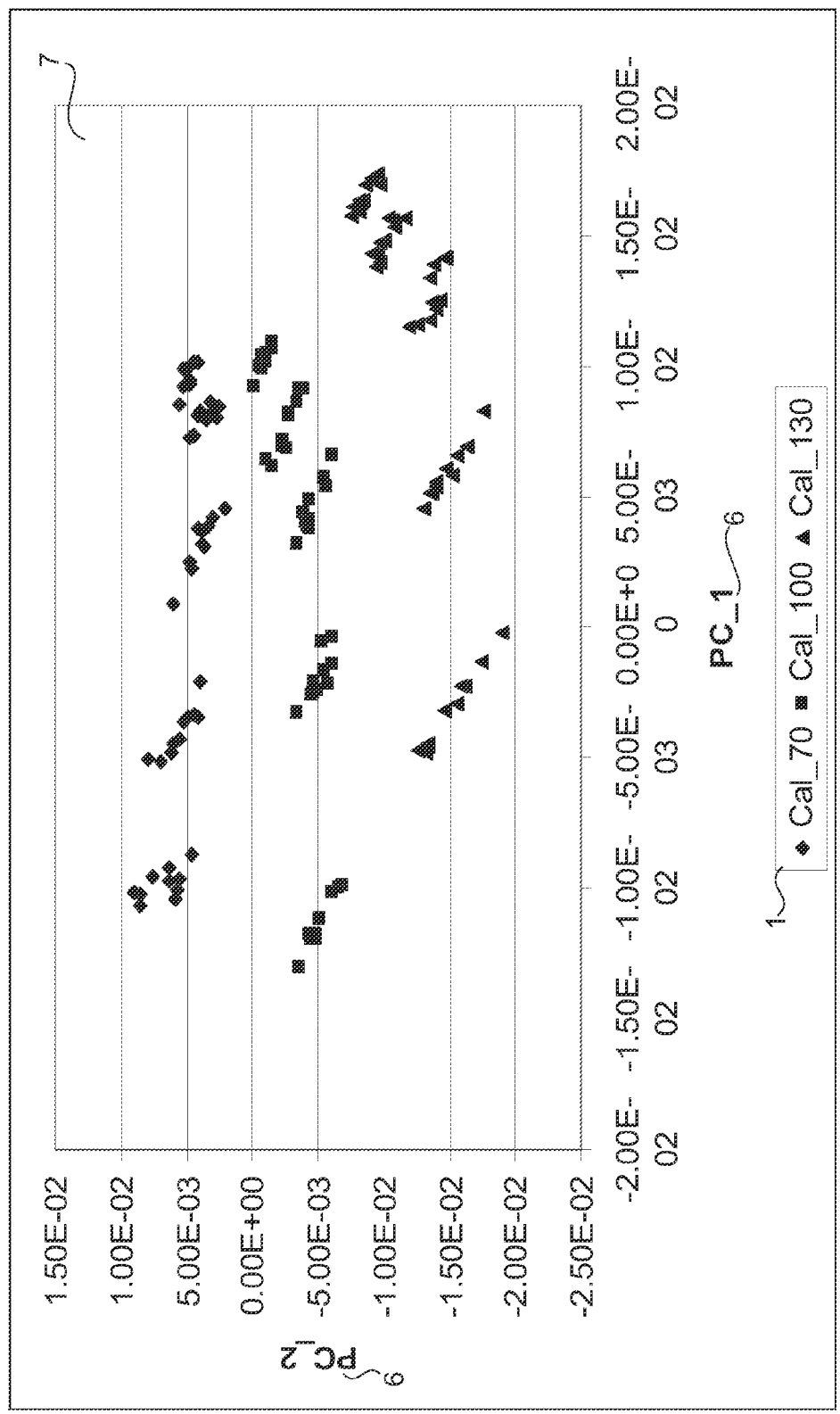
FIG. 1 demonstrates distribution of scores of calibration samples in the two-dimensional PC_1 and PC_2 space.

This invention uses an embodiment that describes the determination of active drug content in pharmaceutical tablets. However, it is understood that this invention can be used for other solid samples in forms and shapes other than pharmaceutical tablets. Unless specifically defined otherwise, the technical and scientific terms used herein have the same meaning as commonly understood by one of the ordinary skills in the art to which this invention pertains. Although any methods and equipments similar or equivalent to those described herein can be used in the practice of the present invention, the preferred methods and equipments are now described.

Pharmaceutical tablets are the most commonly used drug delivery systems, which can be manufactured, stored, distributed, dispensed and administered in a cost effective fashion. As a special category of products, quality of pharmaceutical tablets is strictly regulated. Content uniformity is one of the most important quality attributes. The most commonly used method for CU is liquid chromatography, which is destructive, time consuming and uses large quantity of solvents. By replacing chromatographic methods with NIR methods can speed up pharmaceutical product development, improve quality and lower testing cost. However, the implementation of NIR in pharmaceutical analysis has been hindered by limitations of NIR calibration models, which are sensitive to changes in formulation composition, manufacturing process and other factors. NIR methods are usually developed for late stage products. They have not been widely used for early stage products due to said limitations. The present invention utilizes a very different modeling approach that is more flexible and show wider applicability particularly in early product development.

Calibration Samples

To perform CU analysis by SPCA, a plurality of calibration tablets (samples) 1 is necessary. One way of preparing the tablets is to use the direct compression approach by adequately mixing the drug substance powder with those of the excipients in a blender. Then the homogeneous powder is used to compress the tablets by a Caver Press or other equivalent equipment. Granulations based on the fluid-bed wet granulation process can also be used. The granules that contain nominal quantity of active drug can be spiked with pure drug substance or excipients to alter the drug content. The spiked samples should be thoroughly mixed in a blender. Then the powder mixture is used for preparation of the tablets. Other powders or granulations based on various manufacturing technologies such as high shear granulation and roller compaction can also be used in the similar fashion for preparation of the tablets.

Additional key considerations for the calibration tablets include drug concentration range and number of concentration levels. The recommended concentration range is from 70 to 130% label claim. The recommended concentration level is three or five, which can be set at 70, 100, 130% or 70, 85, 100, 115, 130% label claim, respectively. To further improve accuracy of the SPCA method, additional systematic variations can be introduced by changing and designing the composition and/or physical properties of the plurality of calibration samples 1. One example of relevant physical property is tablet hardness, which is altered by applying different compression force. Another example is by changing composition of excipients. FIG. 11 presents a design of the calibration tablets that have both drug content and compression force changes included. It is recommended that 10 tablets are prepared at each design point.

For the purpose of demonstration, caplet shaped tablets of 250 mg strength (API=42% w/w) were prepared according to FIG. 11 through a direct compression process. The active drug and two excipients were blended in a bin blender for 10 minutes at 25 RPM. Magnesium stearate was then added and the powder mixture was blended for 5 more minutes. Tablets were prepared manually using a Carver Press. The plurality of calibration samples 1 are pharmaceutical tablets with various sizes and shapes that are commonly available in drug stores.

Data Acquisition and Analysis for Calibration Samples

Figure 4:
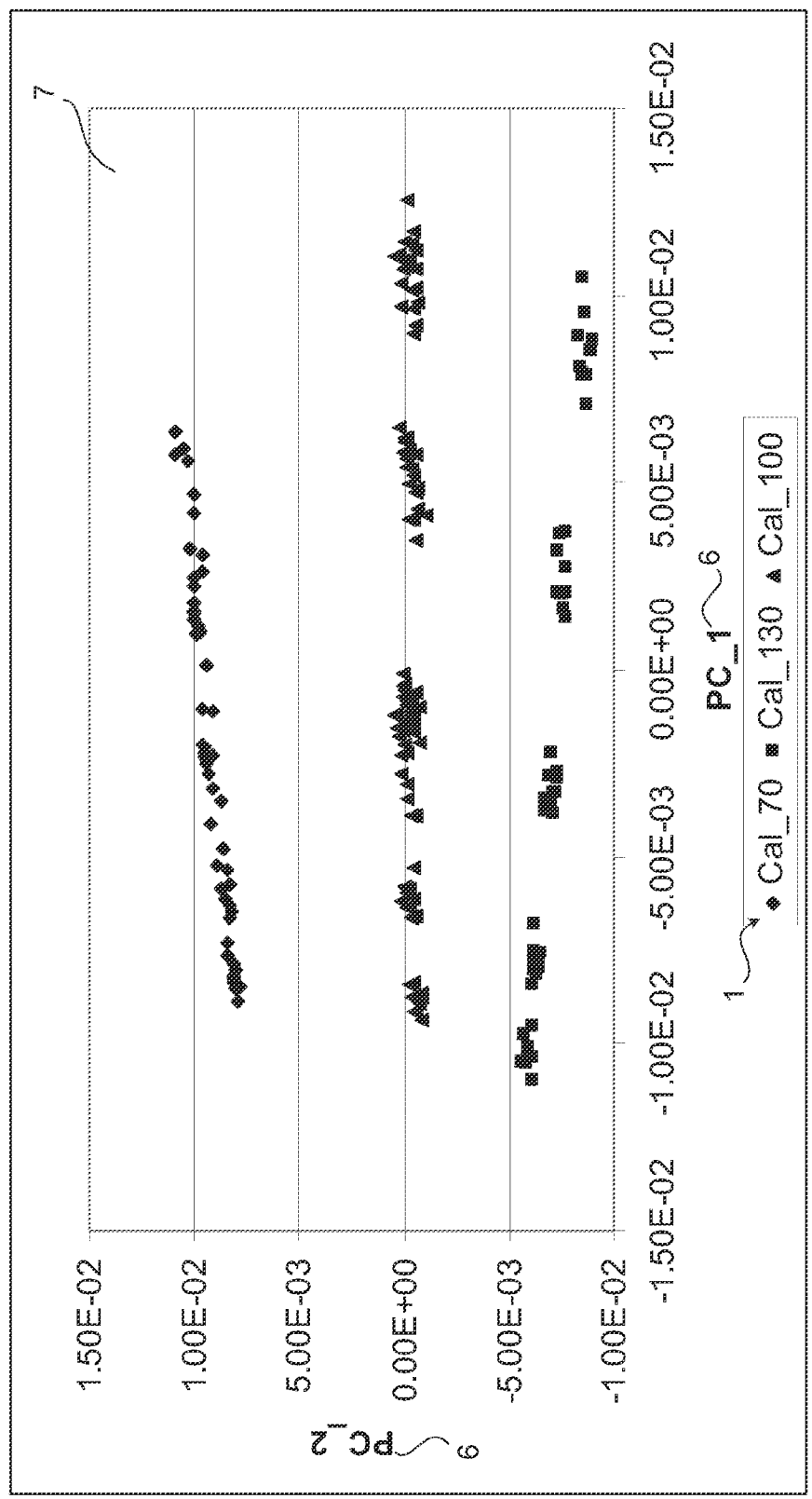
FIG. 4 demonstrates distribution of scores of calibration samples in the two-dimensional PC_1 and PC_2 space after wavelength region and/or range optimization.
Figure 12:
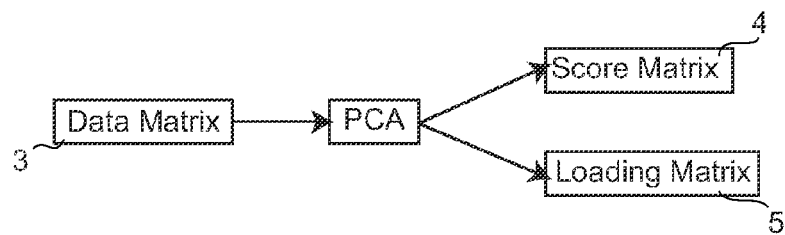
FIG. 12 is the process of obtaining a score matrix and a loading matrix from the data matrix.

The tablets were scanned using a FOSS NIRSystem MasterLab in the transmittance mode with a wavelength range of 800-1650 nm. Then the raw spectra were converted to $1^{st}$ derivative spectra. It is necessary to perform pretreatment before PCA. However, complicated mathematical manipulations of the spectra, including multiplicative scattering correction (MSC) and extended multiplicative scattering correction (EMSC), are not recommended. In reference to FIG. 12, after the pretreatment, data analysis is generally performed according to the following steps: (a) select a wavelength range to produce the first data matrix $X_1$ 3; (b) perform PCA for $X_1$ 3 to obtain the score 4 ($T_1$) and loading 5 ($P_1$) matrices; (c) examine the score and loading plots to evaluate the results (FIG. 1). Steps (a) to (c) are repeated by selecting a different wavelength ranges (and/or region) to produce matrices $X_2$, $X_3$, etc, for analyses until satisfactory results are obtained (FIG. 4).

Figure 2:
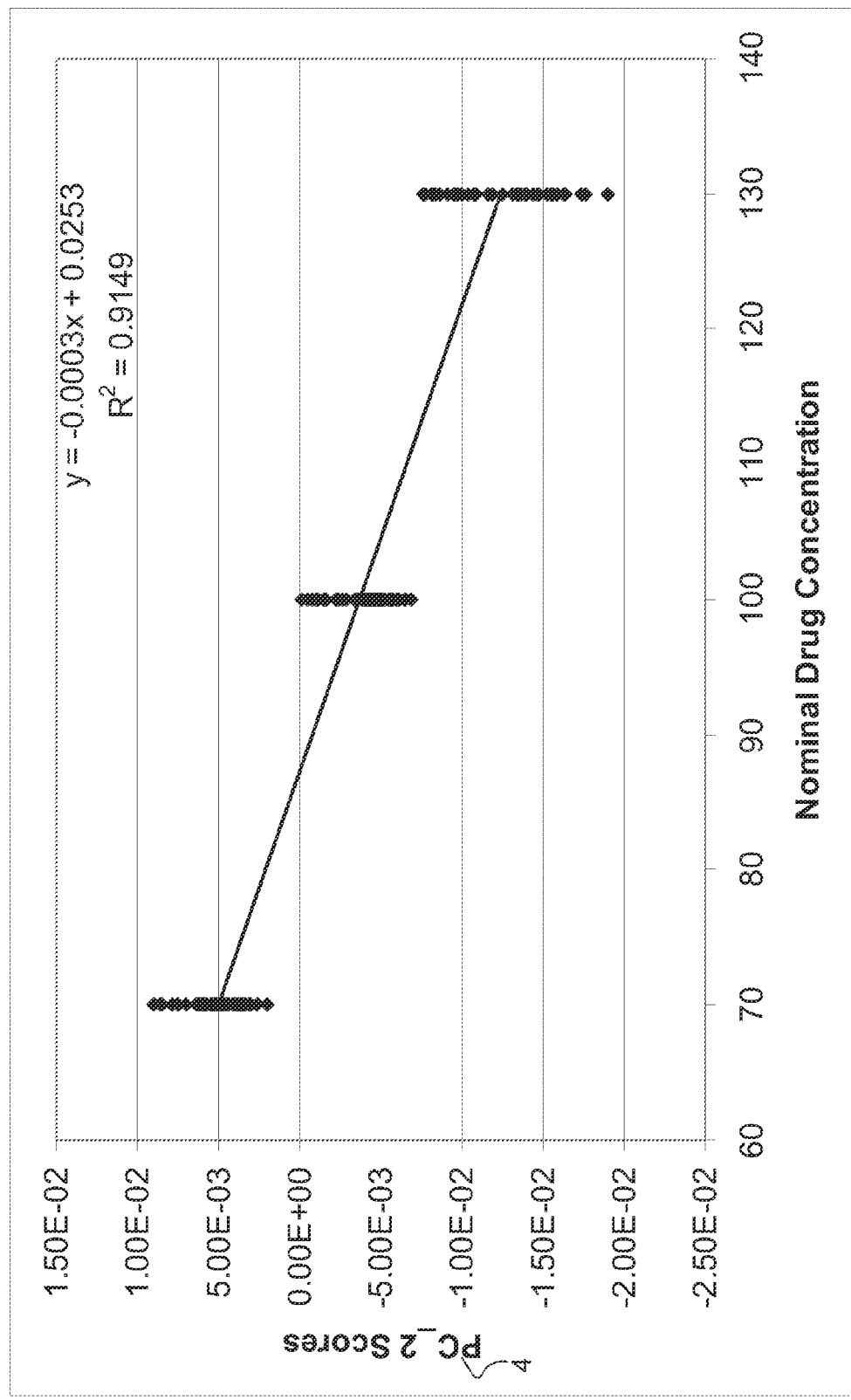
FIG. 2 is a plot showing the correlation between scores (PC_2) of calibration samples and nominal drug concentration.
Figure 3:
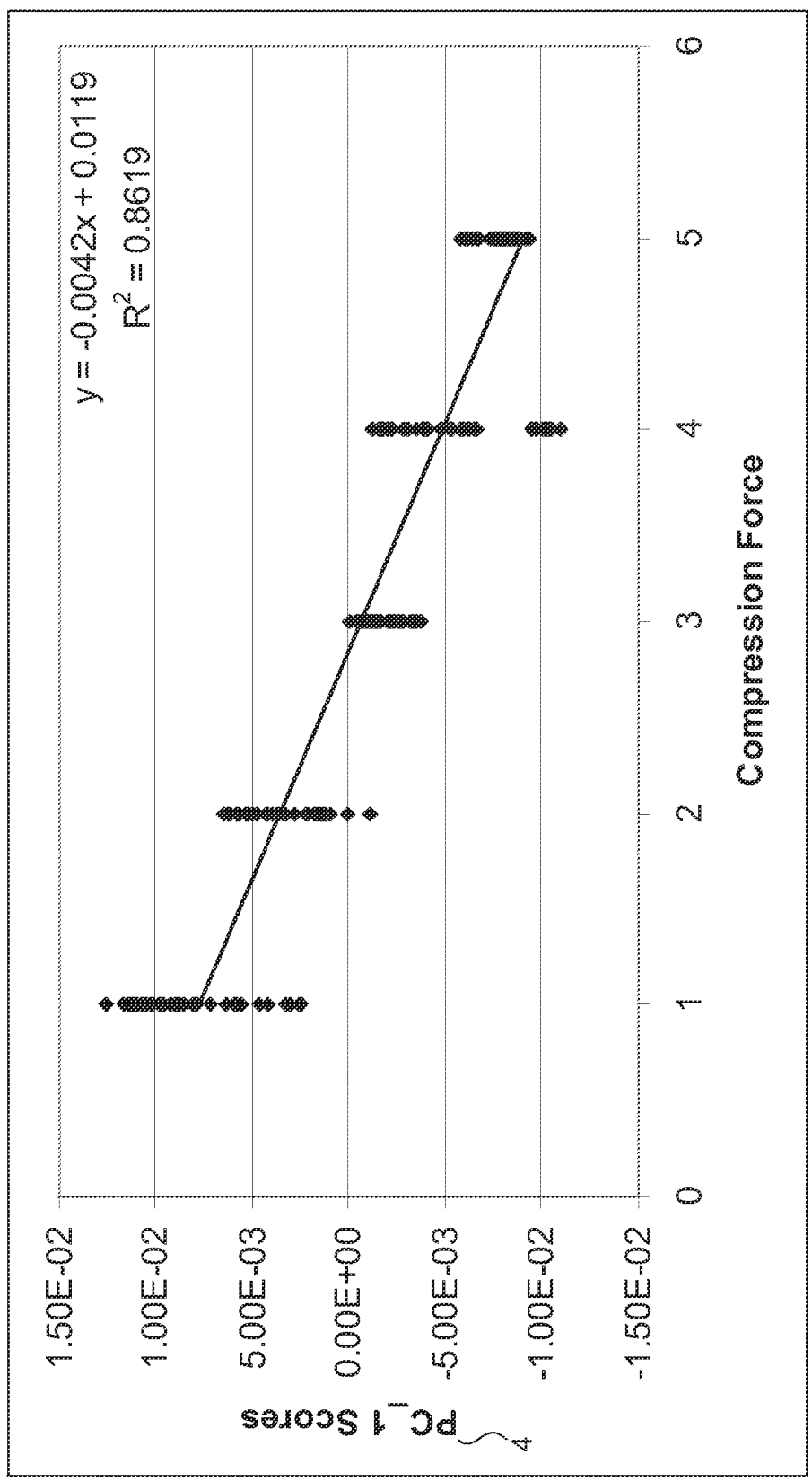
FIG. 3 is a plot showing the correlation between scores (PC_1) of calibration samples and compression forces.

Based on the experimental design in the table in FIG. 11, it is expected that the highest-ranked latent variables used for decomposing matrix $X_1$ should describe variances that are related to drug content and tablets hardness. This is confirmed by FIG. 1, which shows the distribution of PCA scores of the calibration tablets 1 (PC1 and PC2) in the two-dimensional principal component space 7. FIG. 2 shows a correlation between nominal drug concentration and the scores of PC2 whereas FIG. 3 shows a correlation between compression forces and the scores of PC1. However, the correlation in FIG. 2 is not good enough for quantitative determination of the drug content. Mathematically, this implies that the orthogonality between PC1 and PC2 is not genuine, meaning that the NIR signal related to the active drug content was not well separated from that related to the tablet hardness change.

The correlation between drug concentration and scores of PC2 was significantly improved by selecting a narrower wavelength range (800-940 nm, the optimized wavelength range) and repeating the above data analysis step. The result is presented in FIG. 4 and FIG. 5, from which an experienced practitioner in the art can recognize significant improvement of the method.

Figure 5:
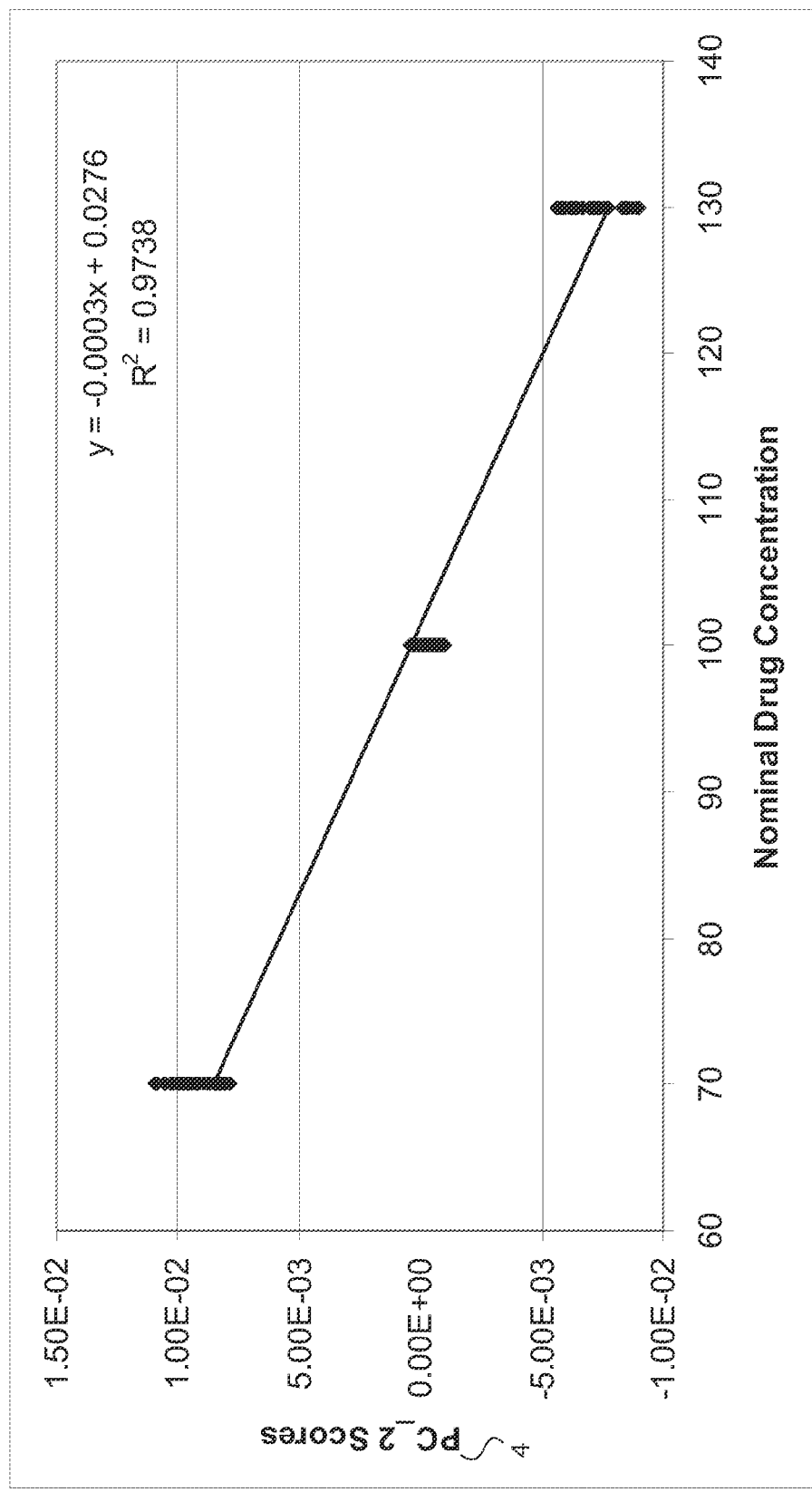
FIG. 5 is a plot showing the correlation between scores (PC_2) of calibration samples and nominal drug concentration after wavelength region and/or range optimization.
Figure 6:
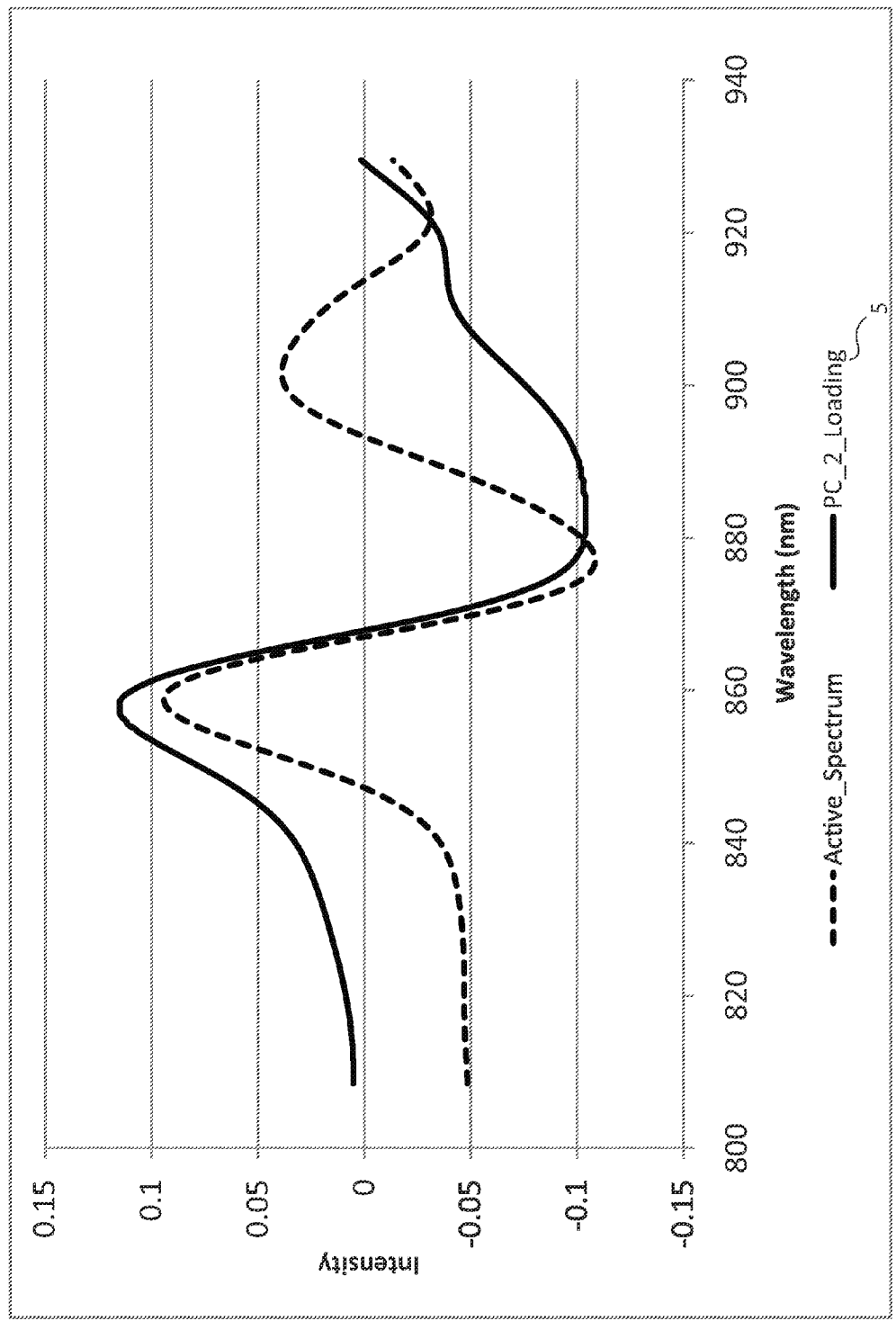
FIG. 6 presents $1^{st}$ derivative NIR spectrum of active drug versus the loading plot (PC_2) of calibration samples.
Figure 7:
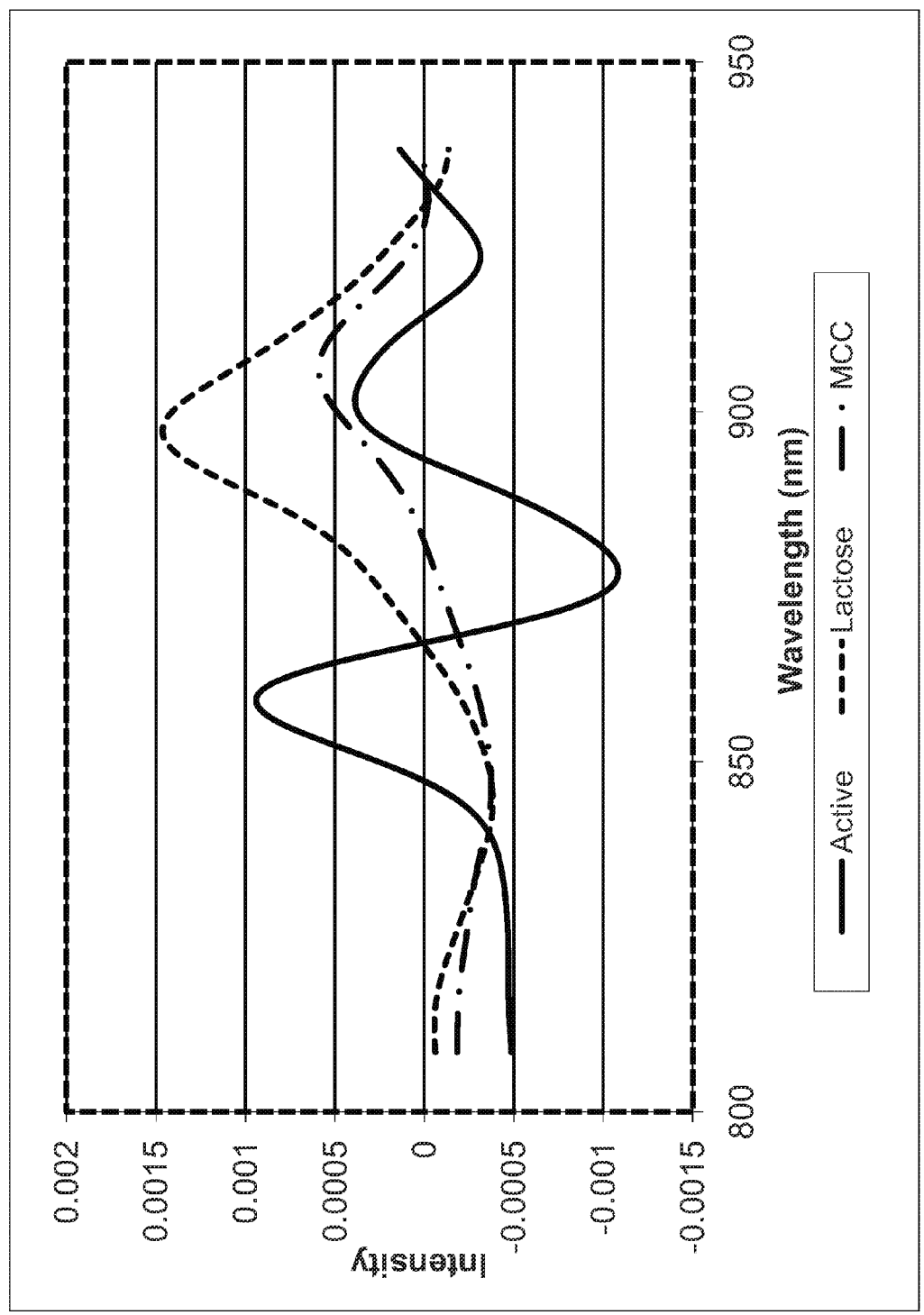
FIG. 7 presents $1^{st}$ derivative NIR spectra of active drug, lactose and microcrystalline cellulose.

The relationship between the latent variable 6 (i.e. PC2) and active drug content can be further verified using two additional criteria. First, there should be certain resemblance between loading plot of the latent variable 6 and the corresponding NIR spectrum of pure drug substance (FIG. 6). It should be noted that the loading plot/spectral match may not be perfect because of the presence of excipients (FIG. 7). Secondly, there should be a correlation between PCA scores of the identified PC and drug concentrations. The relationship can be established using the nominal values or using a reference method (FIG. 2, FIG. 5 and FIG. 9).

To summarize, in developing a calibration model for the SPCA method, a correlation between PCA scores of a particular latent variable and a desired property of pharmaceutical tablets is established using three criteria: (1) a genuine orthogonal distribution of the scores of two latent variables in a two-dimensional space; (2) a correlation between the loading plot of the latent variable and NIR spectrum of the chemical entity of interest; (3) a linear relationship between the scores of the latent variable and nominal concentration values (or reference values) of the chemical entity. These three criteria establish validity of the SPCA method. The nominal drug concentration values can be used as markers for quantitative analysis.

Figure 8:
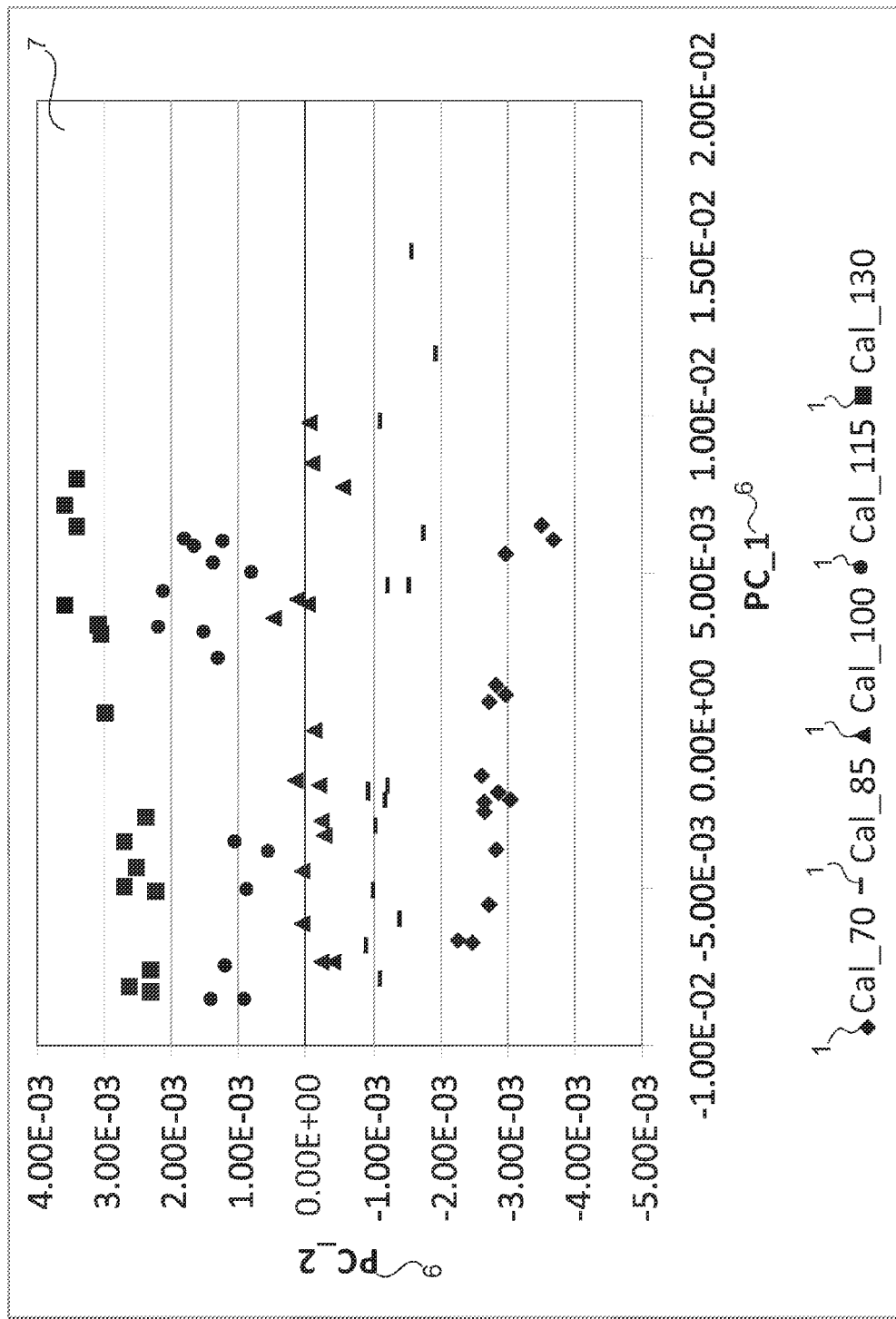
FIG. 8 demonstrates distribution of scores of calibration samples with five drug concentration levels in the two-dimensional PC_1 and PC_2 space.
Figure 9:
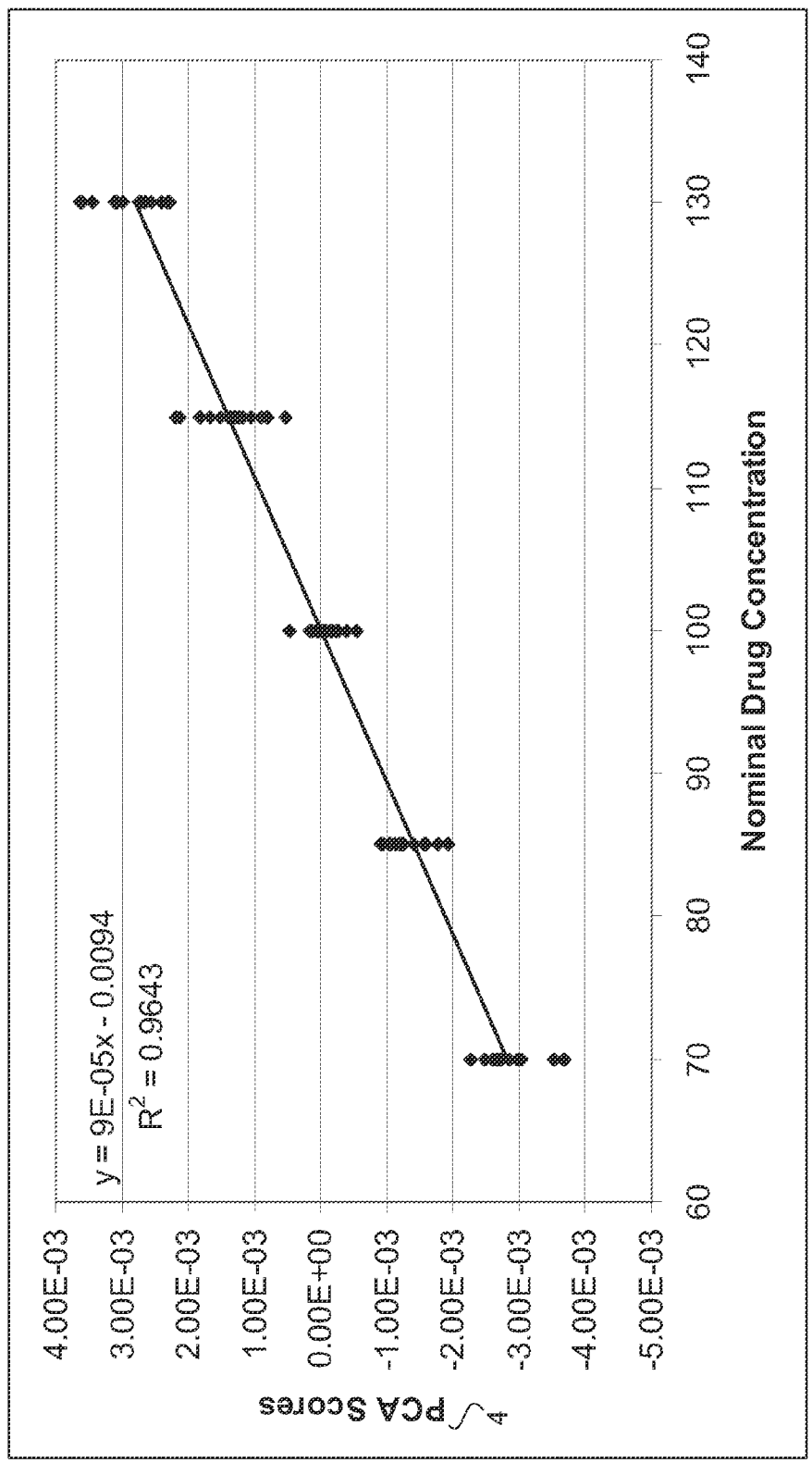
FIG. 9 is a plot showing the correlation between scores (PC_2) of calibration samples with five drug concentration levels and nominal drug concentration.
Figure 10:
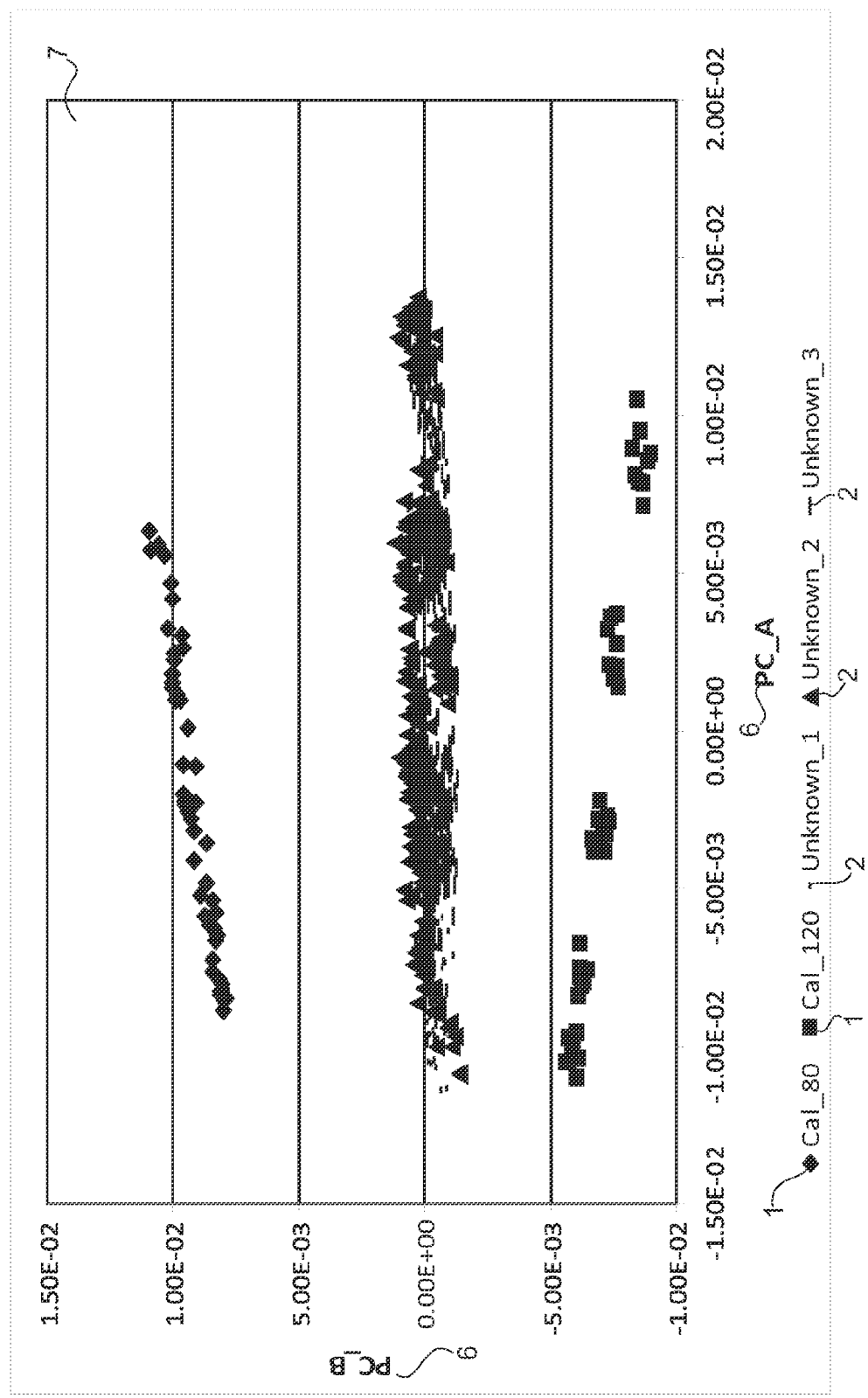
FIG. 10 demonstrates distribution of scores of calibration and unknown samples in the two-dimensional PC_1 and PC_2 space.

The use of five-level calibration tablet set for a SPCA method is illustrated in FIG. 8 and FIG. 9. Again PC1 correlates with tablet hardness whereas PC2 correlates with nominal drug concentration.

Data Acquisition and Analysis for Unknown Samples

Figure 13:
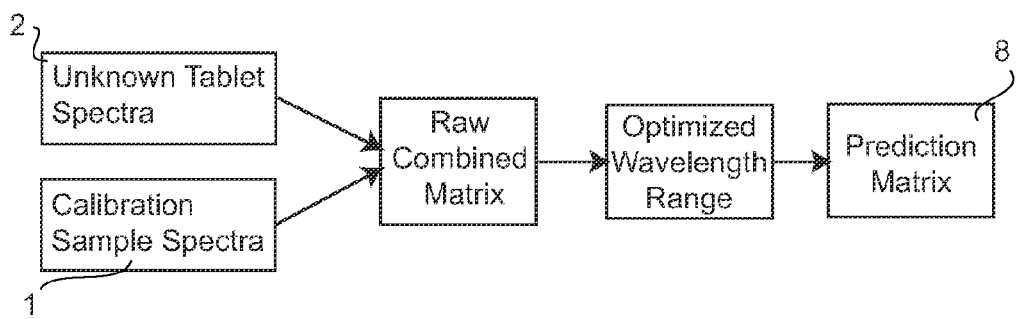
FIG. 13 is the process of obtaining the prediction matrix from the combination of the unknown sample spectra and the calibration sample spectra.
Figure 14:
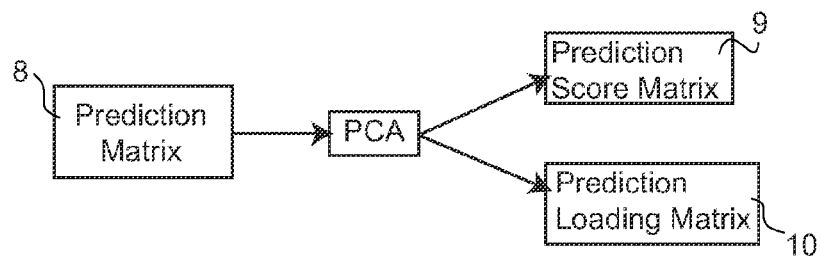
FIG. 14 is the process of obtaining a prediction score matrix and a prediction loading matrix from prediction matrix for the unknown sample.

Unknown tablets 2 of the same size, shape, similar weight and composition as those of above mentioned calibration samples 1 were scanned using a FOSS NIRSystem MasterLab in the transmittance mode with a wavelength range of 800-1650 nm. Then the raw spectra of the unknown tablets 2 were converted to $1^{st}$ derivative spectra, which were further combined with those of the calibration samples 1 as shown in FIG. 13. The combined spectra set of the unknown tablets and the calibration samples 1 was truncated according to the optimized wavelength range (800-940 nm) to form the matrix Xp (or the prediction matrix 8). In reference to FIG. 14, for determining drug content in these unknowns, the following steps are generally followed: (a) using the defined optimized wavelength range to produce the prediction matrix Xp; (b) performing PCA for Xp to obtained the score 9 ($T_p$) and loading 10 ($P_p$) matrices; (c) calculating CU using the regression equations in FIG. 5 and FIG. 9 and the identified PCA scores.

The invention claimed is:

1. A method for determining an active drug concentration in pharmaceutical tablets or powders by using near infrared spectroscopy and supervised principal component analysis, said method comprising the steps of:
   a. designing a plurality of calibration samples with variations in drug concentration, and introducing additional systematic variations by changing the composition of said calibration samples, including changing the composition of excipients, and by changing physical properties of said calibration samples, including changing tablet hardness;
   b. performing spectral pretreatment of acquired near infrared (NIR) spectra without using multiplicative scattering correction (MSC) or extended multiplicative scattering correction (EMSC), and then selecting a wavelength range/region from the spectra to produce data matrix $X_1$;
   c. performing Supervised Principal Component Analysis (SPCA) to decompose matrix $X_1$ in order to obtain a loading matrix $P_1$ and a score matrix $T_1$;
   d. determining the correlation between the Supervised Principal Component (PC) scores and nominal drug concentration;
   e. examining orthogonality of the Supervised Principal Component (PC) scores of desired latent variables in a two-dimensional Principal Component (PC) space, wherein said desired latent variables are the ones that describe the variations of drug concentration in the calibration samples;
   f. evaluating said desired latent variables to determine three criteria: 1) the orthogonality among latent variables is genuine, 2) there is a correlation between a plot of the loading matrix and the NIR spectrum of a chemical entity of interest, and 3) there is a linear relationship between the scores of said latent variables and nominal drug concentration values;
   g. if said three criteria are satisfied, going to step h, if said three criteria are not satisfied, choosing different wavelength ranges and repeating step b, to step f, with new data matrix $X_2$, $X_3$ . . . $X_n$, new loading matrix $P_2$, $P_3$ . . . $P_n$, and new score matrix $T_2$, $T_3$ . . . $T_n$, until said three criteria are satisfied, then going to step h;
   h. performing spectral pretreatment of acquired NIR spectra from unknown samples;
   i. combining the spectra sets of said unknown samples and said calibration samples;
   j. truncating said combined spectra according to the wavelength range determined by steps b, to g, to generate a prediction matrix $X_p$;
   k. performing a Supervised Principal Component Analysis (PCA) with prediction matrix $X_p$ to obtain a loading matrix $P_p$ and a score matrix $T_p$; and
   l. calculating drug content in unknown samples based on said score matrix $T_p$ obtained from said prediction matrix $X_p$.

2. The method as set forth in claim 1, wherein the designed calibration samples are for enhancing the ranking of the desired latent variables used in SPCA.

3. The method as set forth in claim 1, wherein the designed calibration samples are for ensuring genuine orthogonality between scores of two latent variables, wherein the scores from at least one of said latent variables are related to active drug concentration.

4. The method as set forth in claim 1, wherein the designed calibration samples containing designed variations, other than drug concentration, are for improving accuracy of said method.

5. The method as set forth in claim 1, wherein the designed calibration samples are for facilitating quantitative analysis of unknown samples by forming a prediction matrix $X_p$ consisting of NIR spectra of calibration and unknown samples.

6. The method as set forth in claim 1, wherein said calibration samples are prepared using a direct compression approach.

7. The method as set forth in claim 1, wherein said calibration samples are prepared using granulation samples based on a pharmaceutical powder engineering technology selected from the group consisting of fluid-bed wet granulation, or high shear wet granulation.

8. The method as set forth in claim 1, wherein said method development including selection of wavelength range and/or region, determination of orthogonality and prediction of drug concentration in unknown samples is completed by using a computer program.

9. The method as set forth in claim 1, wherein said calibration and unknown samples are pharmaceutical tablets with various sizes and shapes commonly available in drug stores.

10. The method as set forth in claim 1, wherein said calibration and unknown samples are solid samples selected from the group consisting of powders blends, or granulations.

11. The method as set forth in claim 1, wherein the selection of a wavelength range affects the correlation between the drug concentration and score matrix.

12. A method for determining an active drug concentration in pharmaceutical tablets and powders by using Raman spectroscopy and supervised principal component analysis, said method comprising the steps of:
  a. designing a plurality of calibration samples with variations in drug concentration, and introducing additional systematic variations by changing the composition of said calibration samples, including changing the composition of excipients, and by changing physical properties of said calibration samples, including changing tablet hardness;
  b. performing spectral pretreatment of acquired Raman spectra without using multiplicative scattering correction (MSC) or extended multiplicative scattering correction (EMSC), and then selecting a wavelength range/region from the spectra to produce data matrix $X_1$;
  c. performing Supervised Principal Component Analysis (SPCA) to decompose matrix $X_1$ in order to obtain a loading matrix $P_1$ and a score matrix $T_1$;
  d. determining the correlation between the Supervised Principal Component (PC) scores and nominal drug concentration;
  e. examining orthogonality of the Supervised Principal Component (PC) scores of desired latent variables in a two-dimensional Principal Component (PC) space, wherein said desired latent variables are the ones that describe the variations of drug concentration in the calibration samples;
  f. evaluating said desired latent variables to determine three criteria: 1) the orthogonality among latent variables is genuine, 2) there is a correlation between a plot of the loading matrix and the Raman spectrum of a chemical entity of interest, and 3) there is a linear relationship between the scores of said latent variables and nominal drug concentration values;
  g. if said three criteria are satisfied, going to step h, if said three criteria are not satisfied, choosing different wavelength ranges and repeating step b, to step f, with new data matrix $X_2$, $X_3$ . . . $X_n$, new loading matrix $P_2$, $P_3$ . . . $P_n$, and new score matrix $T_2$, $T_3$ . . . $T_n$, until said three criteria are satisfied, then going to step h;
  h. performing spectral pretreatment of acquired Raman spectra from unknown samples;
  i. combining the spectra sets of said unknown samples and said calibration samples;
  j. truncating said combined spectra according to the wavelength range determined by steps b, to g, to generate a prediction matrix $X_p$;
  k. performing a Supervised Principal Component Analysis (PCA) with prediction matrix $X_p$ to obtain a loading matrix $P_p$ and a score matrix $T_p$; and
  l. calculating drug content in unknown samples based on said score matrix $T_p$ obtained from said prediction matrix $X_p$.

13. The method as set forth in claim 12, wherein the designed calibration samples are for enhancing the ranking of the desired latent variables used in SPCA.

14. The method as set forth in claim 12, wherein the designed calibration samples are for ensuring genuine orthogonality between scores of two latent variables, wherein the scores from at least one of said latent variables are related to active drug concentration.

15. The method as set forth in claim 12, wherein the designed calibration samples containing designed variations, other than drug concentration, are for improving accuracy of said method.

16. The method as set forth in claim 12, wherein the designed calibration samples are for facilitating quantitative analysis of unknown samples by forming a prediction matrix $X_p$ consisting of Raman spectra of calibration and unknown samples.

17. The method as set forth in claim 12, wherein said method development including selection of wavelength range and/or region, determination of orthogonality and prediction of drug concentration in unknown samples is completed by using a computer program.

18. The method as set forth in claim 12, wherein said calibration and unknown samples are pharmaceutical tablets with various sizes and shapes commonly available in drug stores.

19. The method as set forth in claim 12, wherein said calibration and unknown samples are solid sample selected from the group consisting of powders blends, or granulations.

* * * * *